(12) United States Patent
Iwanaga et al.

(10) Patent No.: US 8,070,291 B2
(45) Date of Patent: Dec. 6, 2011

(54) FUNDUS CAMERA

(75) Inventors: Tomoyuki Iwanaga, Yokohama (JP); Manabu Wada, Kawasaki (JP); Shinya Tanaka, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/035,877

(22) Filed: Feb. 25, 2011

(65) Prior Publication Data

US 2011/0149243 A1 Jun. 23, 2011

Related U.S. Application Data

(63) Continuation of application No. 12/619,446, filed on Nov. 16, 2009, now Pat. No. 7,918,557.

(30) Foreign Application Priority Data

Nov. 17, 2008 (JP) .................................. 2008-293446

(51) Int. Cl.
*A61B 3/14* (2006.01)

(52) U.S. Cl. ........................................ 351/221; 351/206
(58) Field of Classification Search .................. 351/206, 351/221, 246, 205, 200
See application file for complete search history.

(56) References Cited

U.S. PATENT DOCUMENTS

2008/0212027 A1* 9/2008 Shimizu ........................ 351/206
* cited by examiner

*Primary Examiner* — Hung Dang
(74) *Attorney, Agent, or Firm* — Canon U.S.A., Inc. IP Division (57) ABSTRACT

A fundus camera includes an illumination unit which includes an optical element configured to irradiate an eye fundus with visible light from a position conjugate with an anterior eye portion of an eye to be examined, and an imaging unit configured to take an image of the eye fundus with light which is emitted from the illumination unit and reflected from the eye fundus, wherein the illumination unit includes a blue LED chip and a fluorescent member that is excited by light emitted from the blue LED chip and emits fluorescence, and the fluorescent member is irradiated again with a part of the light reflected by the optical element.

17 Claims, 6 Drawing Sheets

FUNDUS CAMERA

CROSS REFERENCE TO RELATED APPLICATIONS

This application is a Continuation of U.S. patent application Ser. No. 12/619,446 filed Nov. 16, 2009, now U.S. Pat. No. 7,918,557 which claims priority to Japanese Patent Application No. 2008-293446 filed Nov. 17, 2008, each of which are hereby incorporated by reference in their entireties.

BACKGROUND OF THE INVENTION

1. Field of the Invention

The present invention relates to a fundus camera that includes a light-emitting diode for emitting white light as a light source for illuminating a fundus of an eye to be examined.

2. Description of the Related Art

Conventionally, a halogen lamp that emits steady light as an observation light source and a xenon tube that emits pulse light as a photographing light source have been used as a light source of a fundus camera.

Further, an illumination device which uses a white light-emitting diode (LED) as a light source has come to be used instead of a fluorescent lamp or an incandescent lamp. The white LED emits white light and consumes only a small amount of power and generates a small amount of heat. Also in an ophthalmologic apparatus such as a fundus camera, an infrared LED has been used as an auxiliary light source or an index projecting light source for alignment.

Further, a white LED has been employed as a light source of a medical device such as an endoscope. The following patent documents discuss an apparatus which uses white light emitted from a white LED.

In Japanese Patent Application Laid-Open No. 2006-174984, light flux which has a plurality of emission colors is emitted from a plurality of LEDs. The LEDs are disposed in a ring shape toward a concave diffuse-reflective member, and diffused and reflected light flux is brought out from a ring-shaped opening, so that efficiency is improved. Further, the LED has white light and infrared light, and an LED which emits light according to a photographing mode is configured to be switched.

In Japanese Patent Application Laid-Open No. 2007-29726, a plurality of LEDs which are disposed in a ring shape and have different wavelengths is used as a light source of a fundus camera, and has at least one of white light, green light, blue light, and infrared light. Further, at least one of the LEDs is used as a flash light source.

Japanese Patent No. 3409666 discusses a planar light emitting apparatus that irradiates a fluorescent member with blue light emitted from a blue LED. The light emitting apparatus mixes the blue light emitted from the blue LED with fluorescence emitted from the fluorescent member to emit white light.

As described above, a white LED which emits white light has come to be used as an observation or a photographing light source in an ophthalmic photographing apparatus such as a fundus camera.

Figure 10:
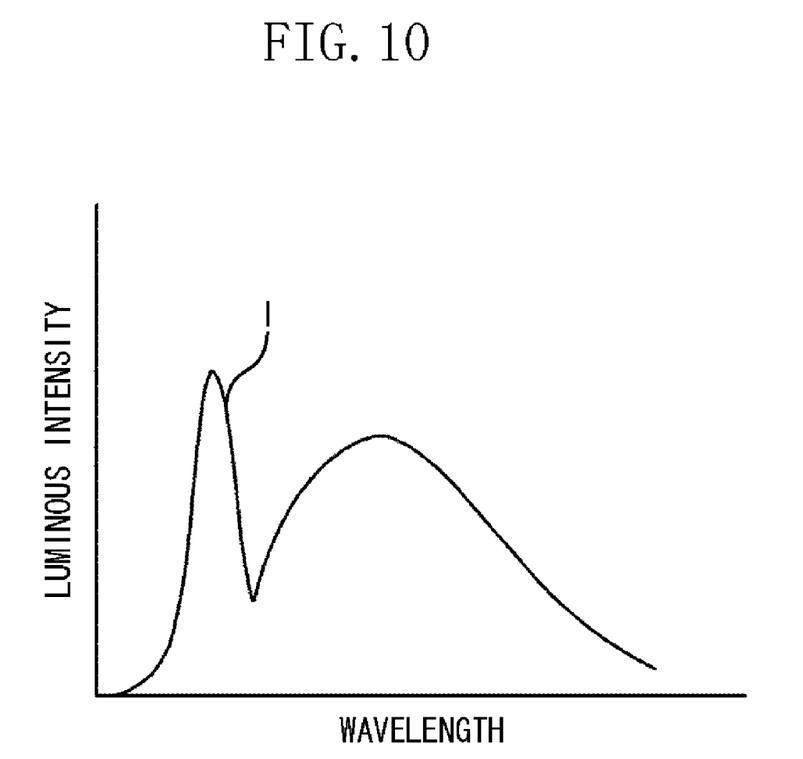
FIG. 10 illustrates spectral intensity of a white LED.

In general, a white LED emits white light by irradiating a yellow fluorescent member with light emitted from a blue LED and mixing the light emitted from the blue LED with the fluorescence emitted from the fluorescent member. Since a part of blue light emitted from the blue LED may be directly emitted without being absorbed by the fluorescent member, a spectral intensity distribution of the white LED is formed as illustrated in FIG. 10. The intensity of green light and red light is lower than that of blue light, so that the color of light becomes pale white. Accordingly, there is a problem in that a color rendering property is lowered.

If photographing is performed using the above-described white LED as a photographing light source, color development is bad in comparison with a conventional halogen lamp or a xenon tube. The color of an eye fundus as an object includes many red components and few blue components. Therefore, an image of the eye fundus shows an unnatural color and use efficiency of the light also deteriorates.

This is because an amount of light which passes through the fluorescent member without exciting the fluorescent member is larger than an amount of light which is emitted from the excited fluorescent member as for the blue light emitted from the blue LED. If the above-described light source is used, generally a known method for maintaining a balance in a color by a balancing filter has been employed. However, in this case, the use efficiency of the light deteriorates.

In recent years, a white LED which has a high color rendering property has been in practical use, in which several kinds of fluorescent members are mixed or an LED emitting a near-ultraviolet ray and a fluorescent member excited by the near-ultraviolet ray are used. Even in the case of the white LED which has a high color rendering property, some light passes through the fluorescent member without exciting the fluorescent member as for light emitted from the LED and energy use efficiency is low.

SUMMARY OF THE INVENTION

The present invention relates to a fundus camera that can obtain an image of an eye fundus which shows a good color development and natural color and has a high use efficiency of the light.

According to an aspect of the present invention, a fundus camera includes an illumination unit which includes an optical element configured to irradiate an eye fundus with visible light from a position conjugate with an anterior eye portion of an eye to be examined, and an imaging unit configured to take an image of the eye fundus with light which is emitted from the illumination unit and reflected from the eye fundus, wherein the illumination unit includes a blue LED chip and a fluorescent member that is excited by light emitted from the blue LED chip and emits fluorescence, and the fluorescent member is irradiated again with a part of the light reflected by the optical element.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EXEMPLARY EMBODIMENTS

Various exemplary embodiments, features, and aspects of the invention will be described in detail below with reference to the drawings.

Figure 1:
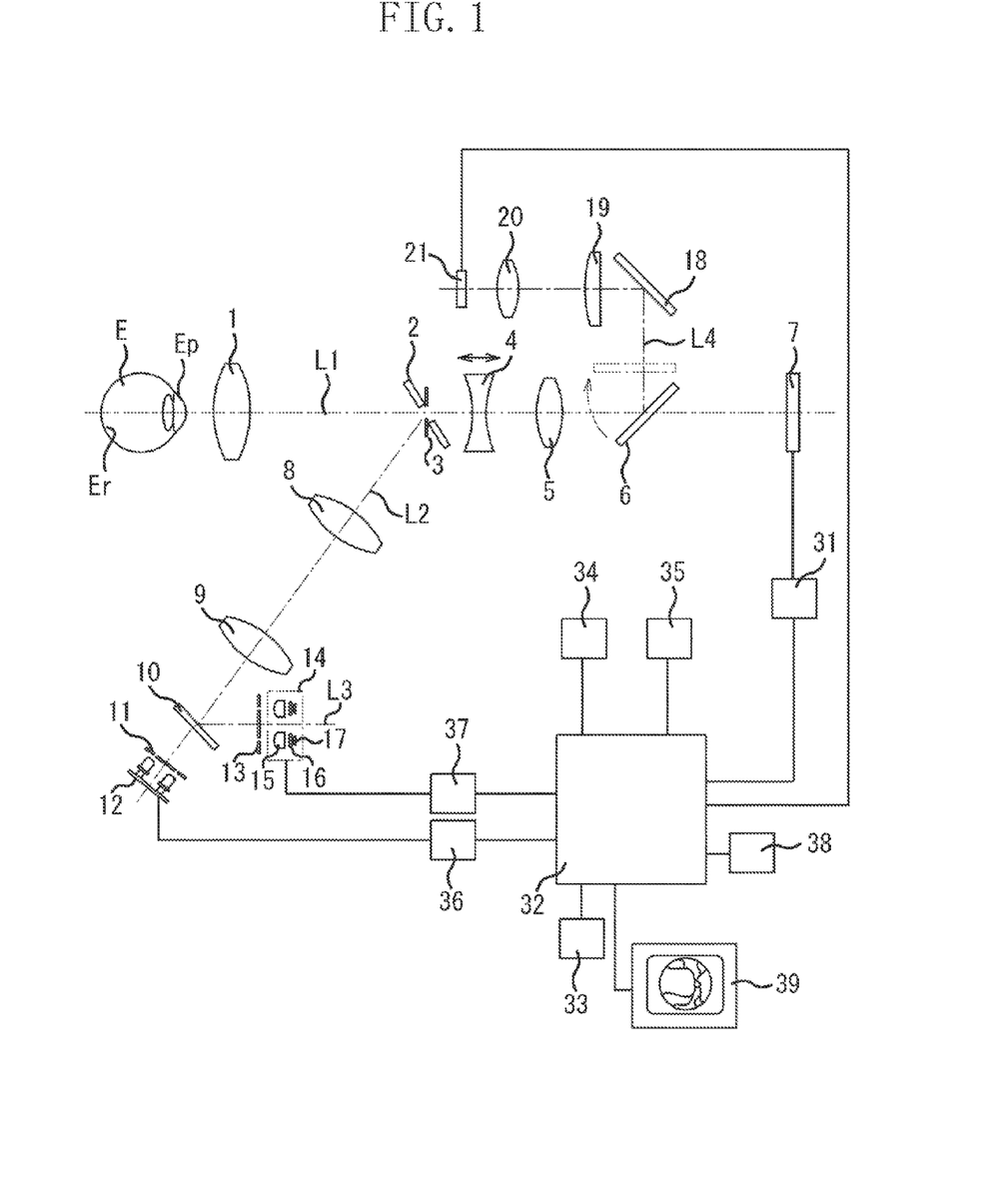
FIG. 1 illustrates a structure of a fundus camera according to a first exemplary embodiment.
Figure 2:
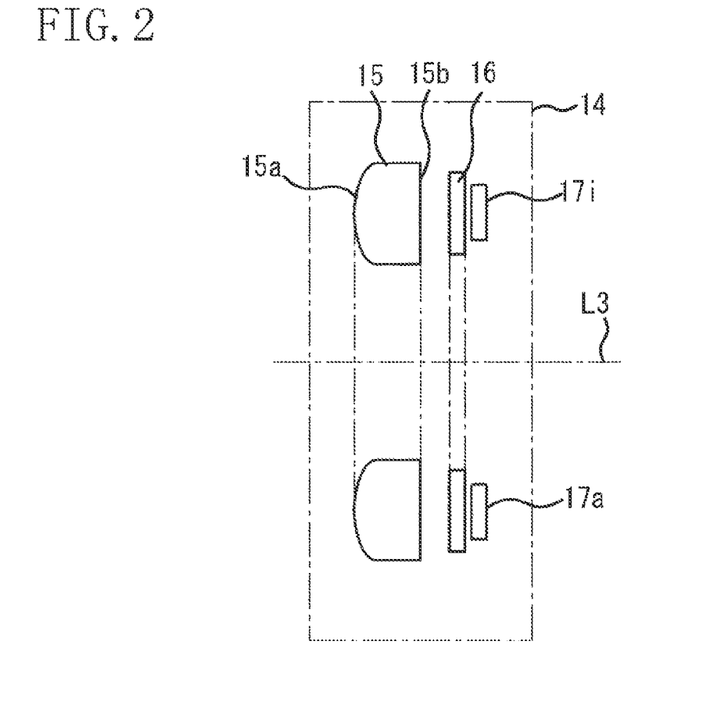
FIG. 2 is an enlarged cross-sectional view of a white LED unit.
Figure 3:
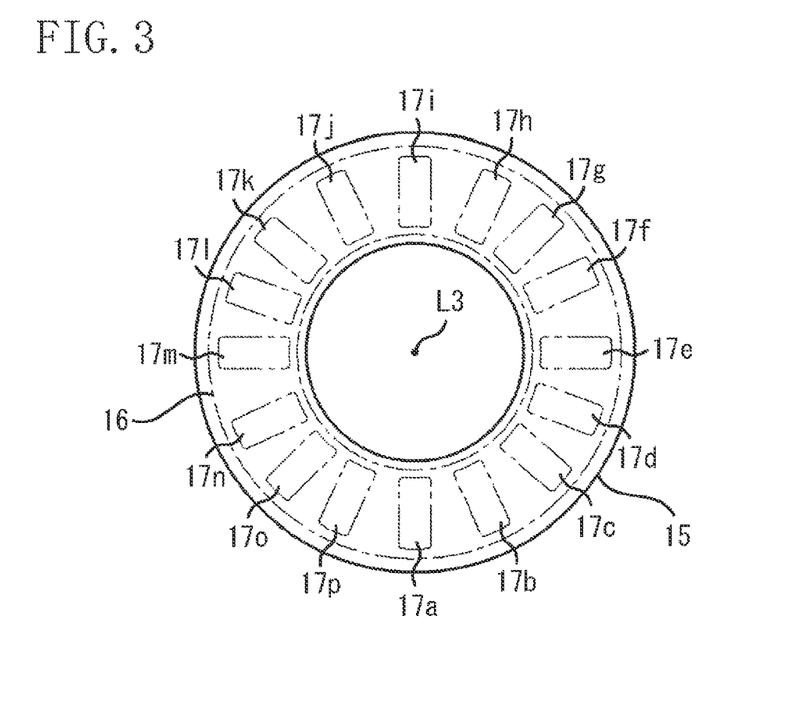
FIG. 3 is a front view of the white LED unit as seen from a ring diaphragm.
Figure 4:
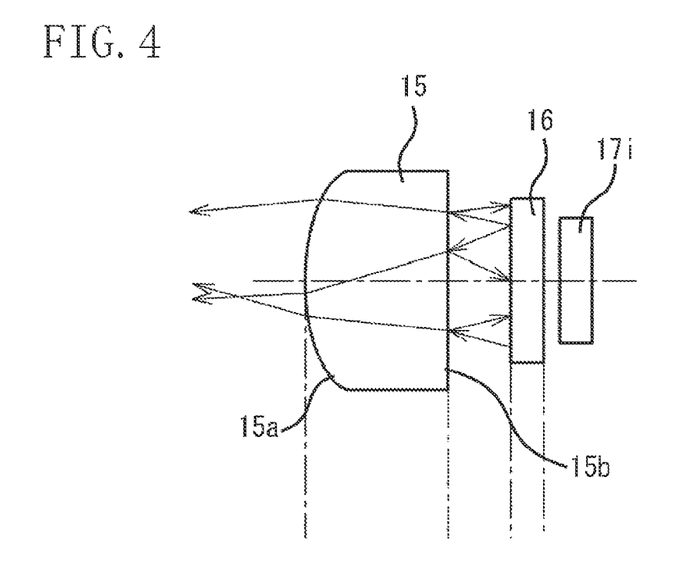
FIG. 4 is an enlarged view of a part of the white LED unit.

FIG. 1 illustrates a structure of a non-mydriatic fundus camera according to a first exemplary embodiment. FIG. 2 is an enlarged cross-sectional view of a white LED unit. FIG. 3 is a front view of the white LED unit. FIG. 4 is an enlarged view of a part of the white LED unit.

An eye fundus imaging optical system includes an objective lens 1, a perforated mirror 2, a photographic diaphragm 3, a focusing lens 4, an imaging lens 5, a flip-up mirror 6, and an image sensor 7 that are sequentially arranged on an optical axis L1 on the front side of an eye E to be examined. The focusing lens 4 is movable in a direction of an optical path, and the image sensor 7 is sensitive to visible light and mainly photographs a still image.

An eye fundus observing-illumination optical system includes lenses 8 and 9, a dichroic mirror 10, a ring diaphragm 11, an infrared LED 12 that are arranged on an optical axis L2 in an incident direction of the perforated mirror 2. The dichroic mirror 10 transmits infrared light and reflects visible light, and the infrared LED 12 emits infrared light. Meanwhile, the ring diaphragm 11 is disposed at a position that is optically conjugate with a pupil Ep of the eye E to be examined via the objective lens 1 and the lenses 8 and 9.

An eye fundus photographing-illumination optical system includes a ring diaphragm 13 and a white LED unit 14 that are provided on an optical axis L3 in an incident direction of the dichroic mirror 10. The ring diaphragm 13 which is a light flux limiting unit is disposed at a position that is optically conjugate with the pupil Ep of the eye E to be examined. The white LED unit 14 is an illumination unit which includes a visible light source that irradiates the vicinity of a conjugated position of an anterior eye portion of the eye to be examined with visible light.

As shown in FIGS. 2 to 4, the white LED unit 14 includes a ring lens 15 formed of a condenser lens. The ring lens 15 has a convex ring shape and a convex refracting power on an optical surface thereof that is formed of a convex surface 15$a$ opposite to one surface of a fluorescent member 16, and the surface of the ring lens facing the fluorescent member 16 is a flat surface 15$b$. The ring-shaped fluorescent member 16 is disposed behind the ring lens 15. Further, a plurality of blue LED chips 17 which is discretely disposed and emits blue light is arranged behind the fluorescent member 16 in a ring shape. For example, sixteen blue LED chips 17$a$ to 17$p$ are used in the present exemplary embodiment.

A dichroic film is formed on the flat surface 15$b$ of the ring lens 15. The dichroic film has a reflectance of 40%, that is, reflects a part of light that has a wavelength illustrated in FIG. 5 and is emitted from the blue LED chips 17$a$ to 17$p$.

In the fundus camera, it is important to form illumination light flux in a ring shape in the vicinity of the pupil Ep of the eye E to be examined and spatially separate the illumination light flux from photographing light flux in order not to reflect reflected light which is not required by the eye E to be examined, on an image of the eye fundus. Further, it is also important to form a light source in a ring shape to efficiently use the light emitted from a light source.

An eye fundus image observing optical system includes a mirror 18, a field lens 19, a television relay lens 20, and an image sensor 21 that are arranged on an optical axis L4 in a reflection direction of the flip-up mirror 6. The image sensor 21 is formed of a charge coupled device (CCD) camera that is used to mainly observe a moving image.

A fundus camera optical unit includes the eye fundus imaging optical system, the eye fundus observing-illumination optical system, the eye fundus photographing-illumination optical system, and the eye fundus image observing optical system that are provided in one camera housing. Further, the fundus camera optical unit is placed on a slide table (not illustrated), and can be aligned with the eye E to be examined.

An output of the image sensor 7 is converted into a digital signal by an analog-digital (A/D) conversion element 31, and is connected to a control unit 32 such as a central processing unit (CPU) that controls the entire apparatus. Further, outputs of the image sensor 21, a character generator 33, an operation unit 34, and a photographing switch 35 are connected to the control unit 32. Outputs of the control unit 32 are connected to an observation light quantity control unit 36 that controls the infrared LED 12, a photographing light quantity control unit 37 that controls the white LED unit 14, a memory 38, and a monitor 39.

Flux of infrared light which is emitted from the infrared LED 12 of the eye fundus observing-illumination optical system is limited by the ring diaphragm 11 during the photographing of the eye fundus. Then, the infrared light passes through the dichroic mirror 10 and forms an image of the ring diaphragm 11 at the position of the perforated mirror 2 through the lenses 9 and 8. Further, the infrared light is reflected in a direction of the optical axis L1 by the perforated mirror 2, forms the image of the ring diaphragm 11 again in the vicinity of the pupil Ep of the eye E to be examined by the objective lens 1, and illuminates an eye fundus Er of the eye E to be examined.

The flux of the light reflected from the eye fundus Er is emitted from the eye E to be examined via an inner area of the image of the ring diaphragm 11 which is formed by the illumination light flux of the pupil Ep. Then, the light enters the flip-up mirror 6 through the objective lens 1, the photographic diaphragm 3, the focusing lens 4, and the imaging lens 5. Further, the light is reflected by the flip-up mirror 6 and the mirror 18, forms an image of the eye fundus Er in the vicinity of the field lens 19, and takes an image through the television relay lens 20 by the image sensor 21. Then, the image of the eye fundus is displayed on the monitor 39.

An operator adjusts the light quantity of the infrared LED 12 by the operation unit 34 so that the image of the eye fundus displayed on the monitor 39 has an appropriate brightness. The operator aligns the eye E to be examined with the fundus camera optical unit by using an operation rod (not illustrated). Further, the operator adjusts the position of the focusing lens 4 in the direction of the optical axis by using a focus knob (not illustrated), thereby adjusting the focus of the displayed image of the eye fundus.

If the operator presses the photographing switch 35 after the completion of the alignment and focus adjustment, the control unit 32 flips up the flip-up mirror 6 up to the position shown by a dotted line, controls the photographing light quantity control unit 37, and causes the white LED unit 14 to emit pulse light.

Blue light which is emitted from the blue LED chips 17a to 17p of the white LED unit 14 includes light that excites the fluorescent member 16 and light that passes through the fluorescent member and is emitted without exciting the fluorescent member 16. The light flux which becomes white light by color mixture between fluorescence from the fluorescent member 16 and the light passing through the fluorescent member without exciting the fluorescent member is condensed by the ring lens 15, and efficiently passes through an opening of the ring diaphragm 13. Further, the fluorescent member 16 is disposed on a focal plane of the ring lens 15.

In the present exemplary embodiment, the fluorescent member 16 has a ring shape. However, the shape of the fluorescent member is not limited to the ring shape, and the fluorescent member may have a shape to efficiently absorb the light emitted from the blue LED chips 17a to 17p that are discretely disposed in a ring shape and emit blue light. For example, if the fluorescent member has a shape to cover the blue LED chips 17a to 17p illustrated in FIG. 3, the fluorescent member has the same function even though having a quadrangular or circular shape. Further, fluorescent members may be disposed right in front of the blue LED chips 17a to 17p, respectively.

The dichroic film which is formed on the flat surface 15b of the ring lens 15 reflects a part of blue light that is directly emitted from the fluorescent member 16 without exciting the fluorescent member 16 to return to the fluorescent member 16, and reuses a part of blue light as excitation light. Light flux which is excited in the fluorescent member 16 by the blue light reflected by the dichroic film and becomes fluorescent passes through the dichroic film again, is condensed by the convex surface 15a, and is used as illumination light flux for photographing the eye fundus.

Since a part of the blue light reflected by the ring lens 15 is used for irradiation again by the fluorescent member 16 as described above, the image of the eye fundus which shows a good color development and natural color is obtained and light is efficiently used.

After the flux of the white light emitted from the white LED unit 14 is limited by the ring diaphragm 13, the white light is reflected in the direction of the optical axis L2 by the dichroic mirror 10 and forms an image of the ring diaphragm 13 on the perforated mirror 2 through the lenses 9 and 8. Further, the white light is reflected in the direction of the optical axis L1 by the perforated mirror 2, forms an image of the ring diaphragm 13 again in the vicinity of the pupil Ep of the eye E to be examined by the objective lens 1, and illuminates the eye fundus Er of the eye E to be examined.

The white light which is reflected and scattered at the eye fundus Er, is emitted from the eye E to be examined via an inner area of the image of the ring diaphragm 13 which is formed by the illumination light flux of the pupil Ep. Then, the white light enters the image sensor 7 through the objective lens 1, the photographic diaphragm 3, the focusing lens 4, and the imaging lens 5. The image of the eye fundus which is photographed by the image sensor 7 is input to the control unit 32 via the A/D conversion element 31, stored in the image memory 38, and displayed on the monitor 39.

Figure 5:
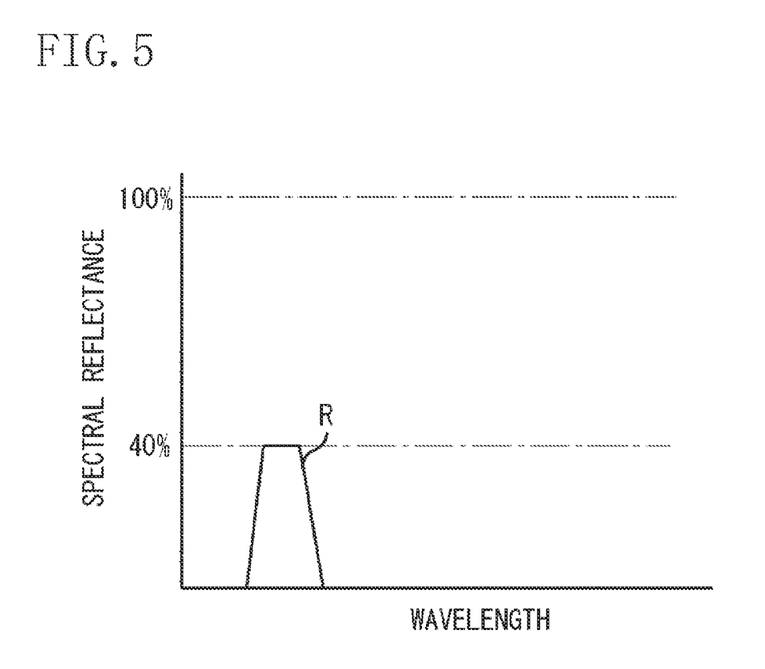
FIG. 5 illustrates spectral characteristics of a dichroic film.
Figure 6:
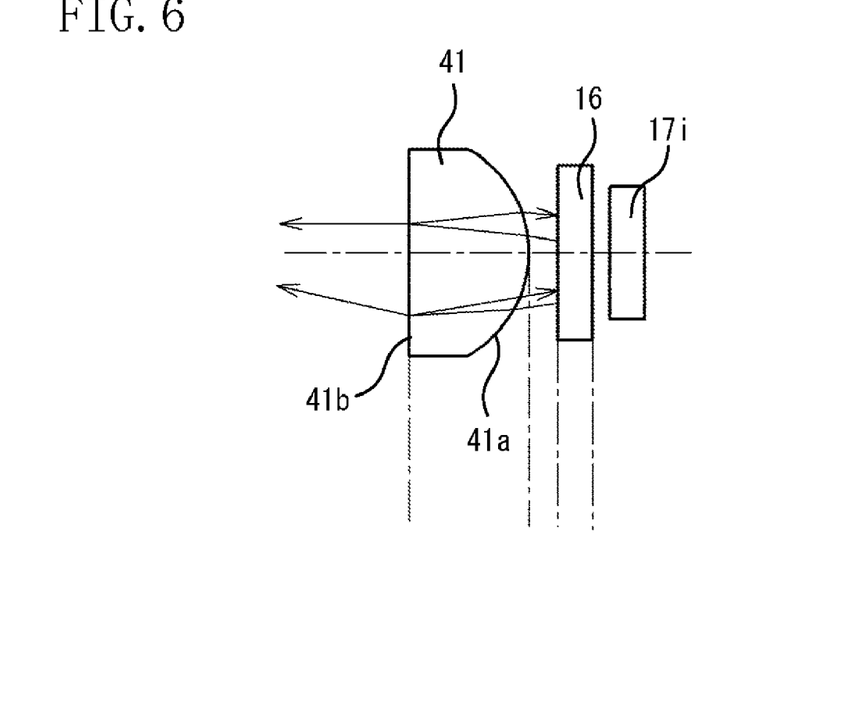
FIG. 6 is an enlarged view of a part of a white LED unit of a second exemplary embodiment.

FIG. 6 is an enlarged view of a part of a white LED unit 14 of a second exemplary embodiment. The similar components as those of the first exemplary embodiment are denoted by the same reference numerals. In the present exemplary embodiment, a ring lens 41 is used as a modification of the ring lens 15 of the first exemplary embodiment. A surface of the ring lens 41 facing the fluorescent member 16 is formed of a convex surface 41a, and an opposite surface thereof is formed of a flat surface 41b. Further, a dichroic film which has the characteristics illustrated in FIG. 5 is formed on the flat surface 41b.

Even in this case, blue light which passes through the fluorescent member 16 without exciting the fluorescent member 16 is reflected by the dichroic film and returns to the fluorescent member 16.

Figure 7:
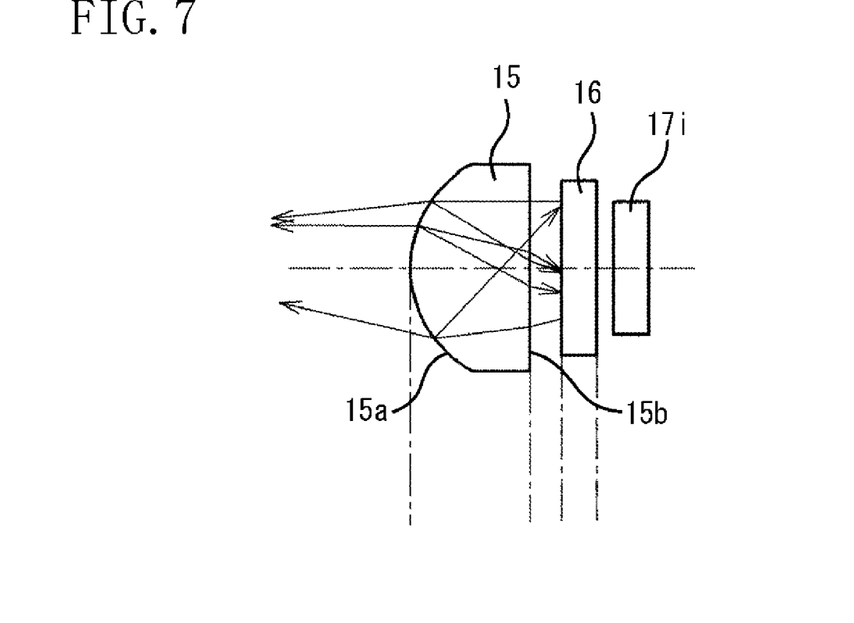
FIG. 7 is an enlarged view of a part of a white LED unit of a third exemplary embodiment.

FIG. 7 is an enlarged view of a part of a white LED unit 14 of a third exemplary embodiment, and a dichroic film which has the characteristics illustrated in FIG. 5 is formed on the convex surface 15a of the ring lens 15 of the first exemplary embodiment. The dichroic film functions as a concave mirror for the blue light that is emitted from the blue LED chips 17a to 17p and emitted from the fluorescent member 16.

According to the above described structure, a part of blue light which passes through the fluorescent member 16 can be returned to the fluorescent member 16 by the concave mirror. Accordingly, use efficiency of the light can be further improved.

Figure 8:
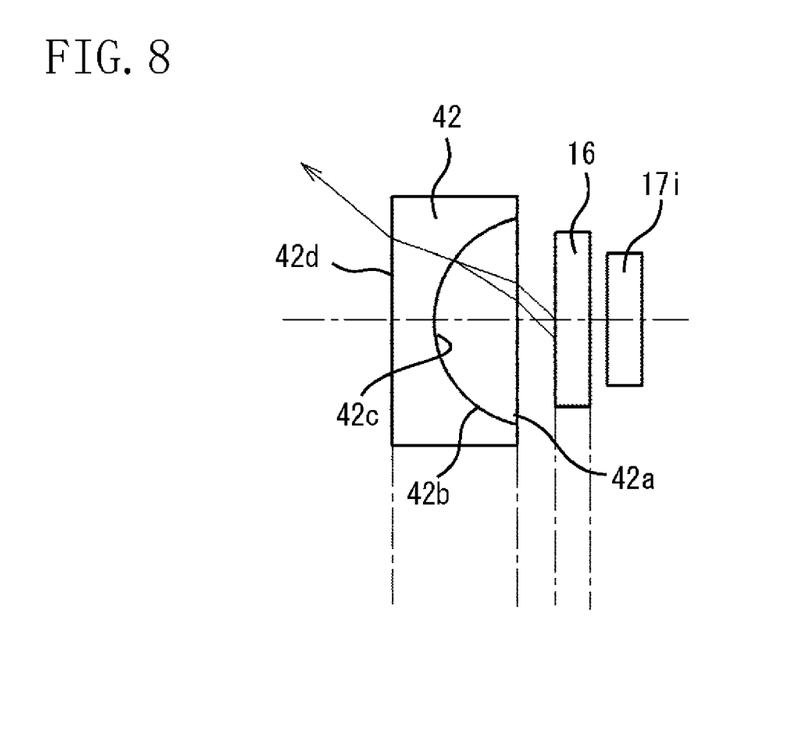
FIG. 8 is an enlarged view of a part of a white LED unit of a fourth exemplary embodiment.

FIG. 8 is an enlarged view of a part of a white LED unit 14 of a fourth exemplary embodiment. A ring combined lens 42 which is formed by bonding two lenses is used in the present exemplary embodiment. One lens of the ring combined lens 42 which faces the fluorescent member 16 has a flat surface 42a on the fluorescent member 16 side and a convex surface 42b on the ring diaphragm 13 side. Further, another lens of the ring combined lens 42 which faces the ring diaphragm 13 has a concave surface 42c that is matched with the convex surface 42b and a flat surface 42d on the ring diaphragm 13 side. A dichroic film which has the characteristics illustrated in FIG. 5 is formed on a bonding surface between the two lenses.

The ring combined lens 42 is formed of an optical element that is formed by bonding two lenses. Since bonding surface of the ring combined lens 42 has a concave surface with respect to the fluorescent member 16 and the dichroic film is formed thereon, the bonding surface between the two lenses can return the blue light other than the blue light which excites the fluorescent member 16 to the fluorescent member 16.

The ring combined lens 42 of the present exemplary embodiment does not have a function of condensing light. However, the ring combined lens can efficiently return the blue light efficiently to the fluorescent member 16. Accordingly, the use efficiency of the light is improved in the fundus camera, so that an image of the eye fundus which shows a good color development can be obtained.

Figure 9:
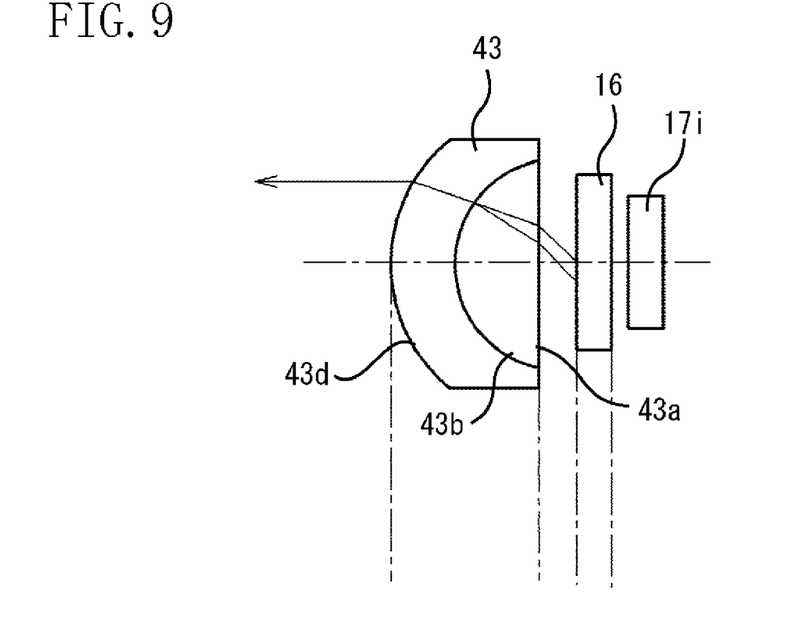
FIG. 9 is an enlarged view of a part of a white LED unit of a fifth exemplary embodiment.

FIG. 9 is an enlarged view of a part of a white LED unit 14 of a fifth exemplary embodiment. A ring combined lens 43 is used in the present exemplary embodiment. In contrast to the ring combined lens 42 of the fourth exemplary embodiment, the ring combined lens 43 has a convex surface 43d which faces the ring diaphragm 13 and is formed on a lens of on the ring diaphragm 13 side of the combined lens.

A dichroic film interposed between the two lenses is formed on a focal plane of the ring combined lens 43, and functions as a concave mirror. The chromatic aberration of light which is not reflected by the bonding surface is corrected by the function of the bonding surface, so that light is condensed by the convex surface 43d and efficiently passes through the opening of the ring diaphragm 13.

In the first to fifth exemplary embodiments, the blue LED chips 17a to 17p have been exemplified as LEDs that emit excitation light of the fluorescent member. However, in recent years, a white LED which has a high color rendering property has been in practical use by mixing several kinds of fluorescent members or by using an LED emitting a near-ultraviolet ray and a fluorescent member excited by the near-ultraviolet ray.

Even in the case of the white LED which has a high color rendering property, there is light which passes through the fluorescent member without exciting the fluorescent member in the light emitted from the LED, that is, excitation light. Thus, energy use efficiency deteriorates. When an LED emitting a near-ultraviolet ray is used as the excitation light, the same effect that is described in the above exemplary embodiments can be obtained by replacing the above-described excitation light, that is, blue light with a near-ultraviolet ray.

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. A fundus camera comprising:
   an illumination unit which includes an optical element configured to irradiate an eye fundus with visible light from a position conjugate with an anterior eye portion of an eye to be examined; and
   an imaging unit configured to take an image of the eye fundus with light which is emitted from the illumination unit and reflected from the eye fundus,
   wherein the illumination unit includes a plurality of blue LED chips and a fluorescent member,
   wherein the fluorescent member has a shape to cover the plurality of blue LED chips, is excited by light emitted from the plurality of blue LED chips, emits fluorescence, and is irradiated again with a part of the light reflected by the optical element.

2. The fundus camera according to claim 1,
   wherein the illumination unit includes a light flux limiting unit that includes a ring-shaped opening and is disposed in the vicinity of the position conjugate with the anterior eye portion of the eye to be examined, and
   wherein the optical element is a convex condenser lens that has convex refracting power to condense light at the ring-shaped opening of the light flux limiting unit.

3. The fundus camera according to claim 1,
   wherein the optical element has a flat surface on a fluorescent member side and a surface which has convex refracting power on a side opposite to the fluorescent member side, and
   wherein the fluorescent member is disposed in the vicinity of a position on a focal plane of the convex refracting power.

4. The fundus camera according to claim 1,
   wherein the plurality of blue LED chips are discretely disposed in a ring shape, and
   wherein the fluorescent member has a ring shape.

5. The fundus camera according to claim 1, further comprising a photographing light quantity control unit configured to cause the illumination unit to emit pulse light.

6. An ophthalmic photographing apparatus comprising:
   an illumination unit configured to irradiate an eye to be examined with visible light; and
   an imaging unit configured to take an image of the eye to be examined with light reflected from the eye to be examined,
   wherein the illumination unit includes a plurality of blue LED chips and a fluorescent member, and
   wherein the fluorescent member has a shape to cover the plurality of blue LED chips, is excited by light emitted from the plurality of blue LED chips and emits fluorescence.

7. The ophthalmic photographing apparatus according to claim 6, further comprising an optical element that reflects a part of light from the fluorescence member.

8. The ophthalmic photographing apparatus according to claim 7, further comprising a photographing light quantity control unit configured to cause the illumination unit to emit pulse light.

9. The ophthalmic photographing apparatus according to claim 6,
   wherein the part of the light reflected by the optical element irradiates the fluorescent member.

10. The ophthalmic photographing apparatus according to claim 6,
    wherein the plurality of blue LED chips are discretely disposed in a ring shape, and
    wherein the fluorescent member has a ring shape.

11. An ophthalmic photographing apparatus comprising:
    an illumination unit configured to irradiate an eye to be examined with visible light; and
    an imaging unit configured to take an image of the eye to be examined with light reflected from the eye to be examined,
    wherein the illumination unit includes at least one near-ultraviolet LED chip and a fluorescent member, and
    wherein the fluorescent member is excited by light emitted from the at least one near-ultraviolet LED chip and emits fluorescence.

12. The ophthalmic photographing apparatus according to claim 11, further comprising:
    an optical element that reflects a part of light from the fluorescence member.

13. The ophthalmic photographing apparatus according to claim 11,
    wherein the part of the light reflected by the optical element irradiates the fluorescent member.

14. The ophthalmic photographing apparatus according to claim 11, wherein the fluorescent member has a shape to cover the at least one near-ultraviolet LED chip.

15. The ophthalmic photographing apparatus according to claim 14,
    wherein the number of the at least one near-ultraviolet LED chip is plural and the plurality of near-ultraviolet LED chips are discretely disposed in a ring shape, and
    wherein the fluorescent member has a ring shape.

16. The ophthalmic photographing apparatus according to claim 14,
    wherein the number of the at least one near-ultraviolet LED chip is plural, and
    wherein the number of the fluorescent member is plural and each of the plurality of the fluorescent members is disposed so as to cover each of the plurality of near-ultraviolet LED chips respectively.

17. The ophthalmic photographing apparatus according to claim 11, further comprising a photographing light quantity control unit configured to cause the illumination unit to emit pulse light.

* * * * *